US011905387B2

(12) United States Patent
Wei et al.

(10) Patent No.: US 11,905,387 B2
(45) Date of Patent: Feb. 20, 2024

(54) FUNCTIONALIZED GRAPHENE OXIDE CURABLE FORMULATIONS

(71) Applicant: PALO ALTO RESEARCH CENTER INCORPORATED, Palo Alto, CA (US)

(72) Inventors: Junhua Wei, Mountain View, CA (US); Gabriel Iftime, Dublin, CA (US); David Mathew Johnson, San Francisco, CA (US); Jessica Louis Baker Rivest, Palo Alto, CA (US)

(73) Assignee: XEROX CORPORATION, Norwalk, CT (US)

( * ) Notice: Subject to any disclaimer, the term of this patent is extended or adjusted under 35 U.S.C. 154(b) by 255 days.

(21) Appl. No.: 17/108,170

(22) Filed: Dec. 1, 2020

(65) Prior Publication Data

US 2021/0079193 A1 Mar. 18, 2021

Related U.S. Application Data

(62) Division of application No. 15/850,871, filed on Dec. 21, 2017, now Pat. No. 10,882,972.

(51) Int. Cl.
| | |
|---|---|
| C08K 3/04 | (2006.01) |
| C01B 32/198 | (2017.01) |
| C08G 59/50 | (2006.01) |
| C08L 63/00 | (2006.01) |
| C08J 5/18 | (2006.01) |
| C08L 33/10 | (2006.01) |
| C07D 303/24 | (2006.01) |
| C07D 493/22 | (2006.01) |
| C07C 69/54 | (2006.01) |
| C08L 33/08 | (2006.01) |
| C08J 5/00 | (2006.01) |
| B29C 64/00 | (2017.01) |
| B33Y 70/10 | (2020.01) |

(52) U.S. Cl.
CPC ............. *C08K 3/042* (2017.05); *B29C 64/00* (2017.08); *B33Y 70/10* (2020.01); *C01B 32/198* (2017.08); *C07C 69/54* (2013.01); *C07D 303/24* (2013.01); *C07D 493/22* (2013.01); *C08G 59/50* (2013.01); *C08J 5/005* (2013.01); *C08J 5/18* (2013.01); *C08L 33/08* (2013.01); *C08L 33/10* (2013.01); *C08L 63/00* (2013.01)

(58) Field of Classification Search
CPC ....... B29C 64/00; B33Y 70/10; C01B 32/198; C07C 69/54; C07D 303/24; C07D 493/22; C08G 59/50; C08J 5/005; C08J 5/18; C08K 3/042; C08L 63/00; C08L 33/10; C08L 33/08

See application file for complete search history.

(56) References Cited

U.S. PATENT DOCUMENTS

| | | | | |
|---|---|---|---|---|
| 3,634,323 A | * | 1/1972 | Moran, Jr. ................. | B32B 7/12 528/111.5 |
| 5,609,960 A | * | 3/1997 | Kasari .................. | C09D 163/00 428/413 |
| 6,335,304 B1 | * | 1/2002 | He ........................ | C08G 59/688 525/534 |
| 9,718,914 B2 | | 8/2017 | Iftime et al. | |
| 10,906,238 B1 | | 2/2021 | Agarwal et al. | |
| 2002/0198290 A1 | * | 12/2002 | Morishita ............ | C09D 5/4492 523/400 |
| 2004/0235980 A1 | * | 11/2004 | Honda .................... | C07C 67/26 526/318 |
| 2008/0071060 A1 | * | 3/2008 | Kobayashi ................ | C08F 2/24 528/392 |
| 2011/0017955 A1 | | 1/2011 | Zhamu et al. | |
| 2014/0126130 A1 | * | 5/2014 | Aurongzeb .......... | H05K 5/0004 361/679.02 |

(Continued)

FOREIGN PATENT DOCUMENTS

| | | |
|---|---|---|
| CN | 108102299 A | 6/2018 |
| CN | 110615971 A | 12/2019 |

(Continued)

OTHER PUBLICATIONS

Machine English translation of JP 2016-195213, Ono et al., Nov. 2016.*
Machine English translation of WO 2015/099371, Choi et al., Jul. 2015.*
Luo, Yuancong et al. "Fabrication of a three-dimensional reinforcement via grafting epoxy functionalized graphene oxide into carbon fibers," Materials Letters 209 (2017), pp. 463-466.
Bao, Chenlu et al. "In situ preparation of functionalized graphene oxide/epoxy nanocomposites with effective reinforcements" J. Materials Chemistry 21 (2011), pp. 13290-132098.

(Continued)

*Primary Examiner* — Patrick D Niland
(74) *Attorney, Agent, or Firm* — Miller Nash LLP

(57) ABSTRACT

A method of producing functionalized graphene oxide includes mixing graphene oxide with a reactive monomer containing at least one epoxy functional group and a secondary functional group that is selected from vinyl, acrylate, methacrylate, and epoxy to form a mixture, adding an activation agent, heating and stirring the mixture, cooling the mixture, separating the particles from the mixture, and drying the particles to produce functionalized graphene oxide. A method of manufacturing a cured polymer resin using functionalized graphene oxide includes mixing functionalized graphene oxide with a resin precursor to produce a functionalized graphene mixture, wherein the particles contain functional groups nearly identical to, or identical to, a polymer precursor material, adding a curing initiator to the functionalized graphene mixture and mixing to produce a formulation, depositing the formulation into a desired shape, and curing the formulation to form a polymer having functionalized graphene oxide groups in a base polymer material.

12 Claims, 9 Drawing Sheets

(56) References Cited

U.S. PATENT DOCUMENTS

| | | |
|---|---|---|
| 2016/0193751 A1 | 7/2016 | Humfeld |
| 2016/0200920 A1* | 7/2016 | Cauchon ............... C09D 7/68 |
| | | 252/511 |
| 2019/0194417 A1 | 6/2019 | Wei et al. |

FOREIGN PATENT DOCUMENTS

| | | | |
|---|---|---|---|
| JP | 2016-195213 | * | 11/2016 |
| WO | WO 2015/099371 | * | 7/2015 |

OTHER PUBLICATIONS

Lu, Shaorong et al. "Epoxy nanocomposites filled with thermotropic liquid crystalline epoxy grafted graphene oxide" RCS Advances 3 (2013) pp. 8915-8923.

Kowalczyk K. and Spychaj, T. "Ionic Liquids as Convenient Latent Hardeners of Epoxy Resigns" Polimery, 48:11-12, (Jan. 1, 2003) pp. 833-835.

Li et al. "Synthesis and characterization of reinforced acrylate photosenstive resin by 2-hydroxyethyl methacrylate-functionalized graphene nanosheets for 3D printing" J. Materials Science (2018) 53, pp. 1874-1886.

Xia et al. "Functionalied graphene serving as free radical scavenger and corrosion protection in gamma-irradiated epoxy composites" Carbon 101 (2016), pp. 315-323.

Wan et al. "Grafting of expoxy chains onto graphene oxide for epoxy composites with improved mechanical and thermal properties," Carbon 69 (2014), pp. 467-480.

Li et al. "Control of the functionality of graphene oxide for its application in epoxy nanocomposites" Polymer 54 (2013) pp. 6437-6446.

Rafiee, M.A. et al. "Enhanced Mechanical Properties of Nanocomposites at Low Graphene Content", ASC NANO, 2009, pp. 3884-3890.

Yu et al., Enhanced Thermal Conductivity in a Hybrid Graphite Nanoplatelet—Carbon Nanotube Filler for Epoxy Composites, Adv. Mater. 2008, 20, 4740-4744.

Im et al., Thermal conductivity of a graphene oxide-carbon nanotube hybrid/epoxy composite,, Carbon 50 (2012) 5429-5440.

Li et al., Carbon nanotube-graphene nanoplatelet hybrids as high performance multifunctional reinforcements in epoxy composites, Composites Science and Technology 74 (2013) 221-227.

Yue et al., Epoxy composites with carbon nanotubes and graphene nanoplatelets—Dispersion and synergy effects, Carbon 78 (2014) 268-278.

Qi et al., Synergistic effect of functionalized graphene oxide and carbon nanotube hybrids on mechanical properties of epoxy composites, RSC Adv., 2018, 8, 38689.

U.S. Appl. No. 17/340,770, filed Jun. 7, 2021.

* cited by examiner

FUNCTIONALIZED GRAPHENE OXIDE CURABLE FORMULATIONS

CROSS REFERENCE TO RELATED APPLICATION

This application is a divisional of U.S. patent application Ser. No. 15/850,871 filed Dec. 21, 2017, which is incorporated herein by reference in its entirety.

TECHNICAL FIELD

This disclosure relates to composite polymer materials, more particularly composite polymer materials including functionalized graphene oxide.

BACKGROUND

Graphene and graphene oxide particles have exceptional mechanical properties such as tensile strength up to 130,000 MPa and Elastic Modulus up to 1000 GPa. For this reason, they have drawn significant attention as fillers in polymer composites with the expectation that they would produce polymer composites with mechanical properties far exceeding those of the base polymer materials. However translation of these properties into macroscopically assembled structures has not yet been demonstrated. Typical values for dispersed graphene-reinforced epoxy composite structures are modest, <70 MPa tensile strength and 2.5-3.5 GPa elastic modulus, respectively, which are orders of magnitude lower than those of graphene [M. A. Rafiee et al. ACS NANO, (2009), 3884].

Particularly, one of the outstanding challenges in conventional graphene filled polymer composites has been the difficulty to achieve composites with simultaneously increased elastic modulus and strength. Typically, the addition of graphene particles achieves easily an increase in the material's stiffness, measured by the elastic modulus, but at the cost of decreasing the composite's strength when compared with the base polymer material. As a result, such composites are brittle. Our understanding is that strength loss takes place by two main mechanisms. First, particle aggregation, meaning poor dispersion, and poor particle polymer interface create regions where mechanical failure occurs. Second, the growth of the polymer chains during curing is interrupted at the interface with the reinforcing particles. Shorter polymer chains generally produce polymer structures with reduced strength. To address this challenge, U.S. Pat. No. 9,718,914 on 1 Aug. 2017 disclosed structured hybrid chemically linked graphene/polymer networks wherein functionalized reactive graphene particles are incorporated as "monomers" into the cured composite material. Directed chemical linkage of the functionalized graphene enables the in-situ building of organized structures, which resemble woven carbon fibers with enhanced mechanical strength when compared with the randomly dispersed non-bonded graphene particle composites.

However, an outstanding challenge which prevents fabrication of graphene/polymer composites with even further increased mechanical properties remains the poor dispersibility of the functionalized graphene into the polymer base material. This limits the concentration of graphene particles into the formulation with the net result of limited achievable mechanical properties. GO is notoriously difficult to disperse in organic polymer formulations. Because the chemical nature of GO differs from the polymer precursor, GO particles aggregate in the polymer matrix and produce poor quality composites. Current solution to this problem consist in using solvents that solubilize both the GO and the polymer precursor. However, the solvent selection is very limited and the process is energy intensive, lengthy and uses large amounts of solvent.

Dispersing GO in high concentrations in polymers becomes very difficult. Typical GO formulations incorporate up to 5% GO. Filling higher concentrations of GO typically does not result in increased mechanical properties, and in some cases results in decreased properties because of the aggregation of the GO particles. Graphene/polymer composites with significantly higher mechanical properties may be achieved with high content dispersed exfoliated graphene polymer composites.

Therefore, a need exists for a method that produces exfoliated functionalized GO particles that can be easily dispersed into and have high compatibility with the polymer base material to enable high content graphene/polymer composites.

SUMMARY

According to aspects illustrated here, there is provided a method of producing functionalized graphene oxide that includes mixing graphene oxide with a reactive monomer containing at least one epoxy functional group and a secondary functional group that is selected from vinyl, acrylate, methacrylate, and epoxy to form a mixture, adding an activation agent, heating and stirring the mixture, cooling the mixture, separating the particles from the mixture, and drying the particles to produce functionalized graphene oxide.

According to aspects illustrated here, there is provided a method of manufacturing a cured polymer resin using functionalized graphene oxide that includes mixing functionalized graphene oxide with a resin precursor to produce a functionalized graphene mixture, wherein the particles contain functional groups nearly identical to, or identical to, a polymer precursor material, adding a curing initiator to the functionalized graphene mixture and mixing to produce a formulation, depositing the formulation into a desired shape, and curing the formulation to form a polymer having functionalized graphene oxide groups in a base polymer material.

DETAILED DESCRIPTION OF THE EMBODIMENTS

The embodiments here provide a novel, curable formulation with exfoliated functionalized graphene oxide particles, a curing initiator and a polymer precursor wherein the graphene oxide particles contain functional groups that are highly identical to a precursor polymer material. Because of the identical chemical nature of the functional groups attached onto the graphene oxide particles, functionalized graphene oxide particles disperse easily at high concentration in the polymer precursors and produce highly dispersed and high graphene content cured structures. Typically, the functionalized graphene oxide particles result from reacting carboxyl and hydroxyl groups present on the graphene oxide with an epoxy reagent that contains functional groups that are similar in chemical nature to the polymer matrix precursors used in the graphene/polymer composite formulation.

Figure 1:
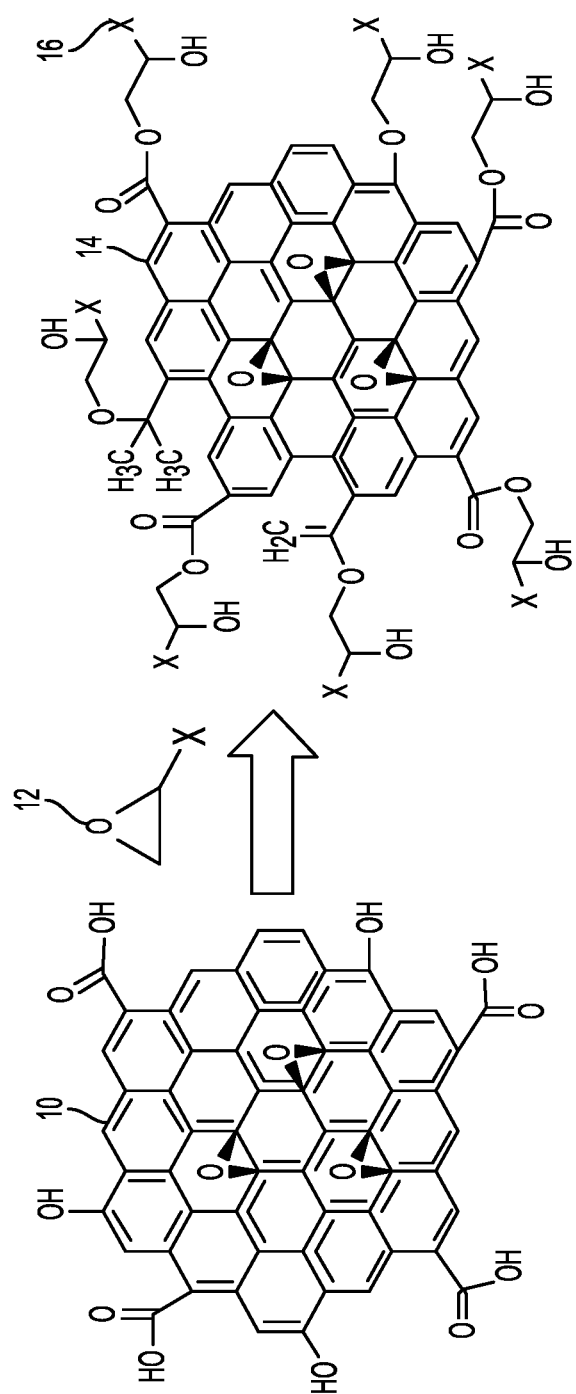
FIG. 1 shows a diagram of an embodiment of a method of synthesizing functionalized graphene oxide using epoxy coupling functional molecules.

FIG. 1 shows a graphical representation of the process for fabrication of functionalized graphene oxide particles. Graphene oxide 10 undergoes bonding between the epoxy groups such as 12 using epoxy reagents. The functionalized graphene oxide particles are then used to fabricate high concentration and highly dispersed graphene oxide into polymer precursor formulations that are easy to apply and cure. The epoxy functionalized graphene oxide 14 has functional groups shown in the diagram as X. The X groups enable the fabrication of formulations containing high concentration and highly dispersed graphene oxide in polymer precursors. Formulations having functionalized graphene oxide particles in concentrations comprised in a range from 0.1% to about 80% can be achieved. Particularly, concentrations higher than of 20% are achievable.

Another benefit of functionalized graphene oxide (FGO) when compared with nonfunctionalized GO lies is the higher degree of cure and lower activation energy for curing. The functional groups present on the FGO are identical to those of the reactive precursors in the base material and they cure at the same time with the polymer precursor. This allows rapid creation of a network of chemically linked GO networks bonded by the polymer precursor linker.

Figure 2:
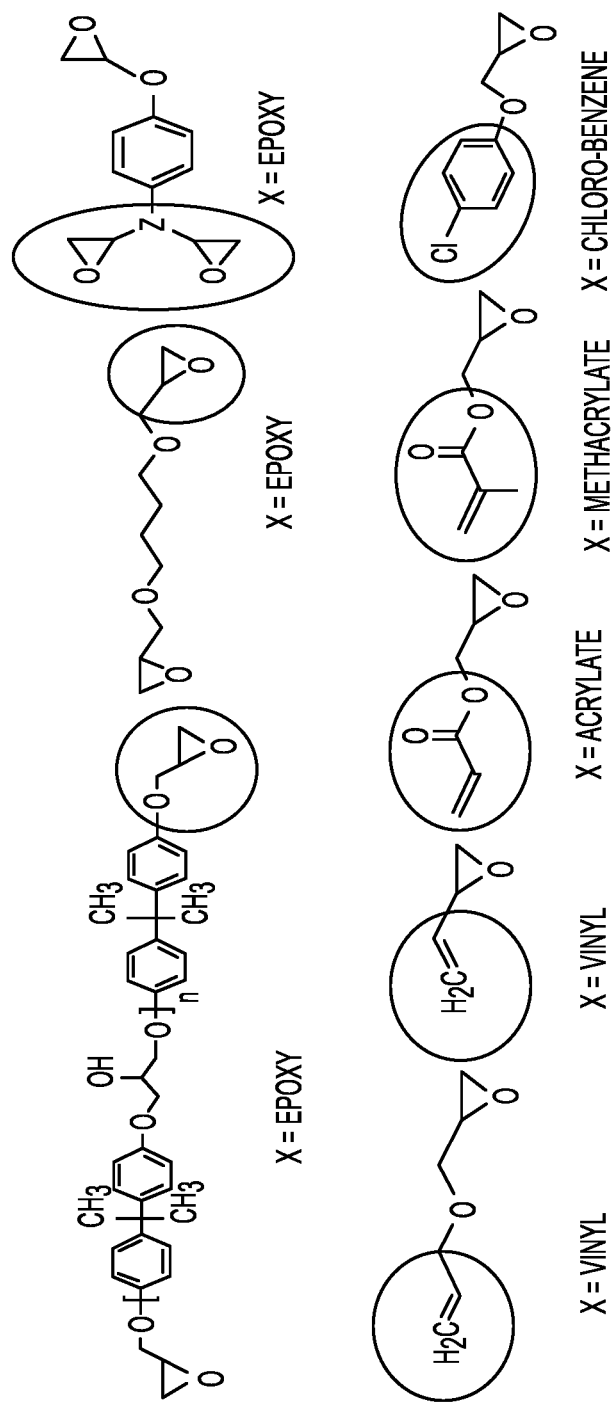
FIG. 2 shows a diagram of embodiments of functional molecules for polymer precursors. The circled areas in the figure represent functional groups available for chemical linking of functionalized graphene oxide particles.

The X group may consist of any group that has a similar chemical nature to the polymer precursor base material. For example, it may consist of an epoxy group, if the polymer precursor consists of an epoxy material. It may also consist of radical polymerizable material such as a vinyl group when the precursor is a vinyl monomer. It may also consist of an acrylate or methacrylate when fabricating cured acrylic or methacrylic composites. FIG. 2 shows some examples of possible X groups. Suitable examples of epoxy monomer precursors include difunctional epoxies such as bisphenol A diglycidyl ether and analogues. According to description in FIG. 2, one of the epoxy groups is used for linking to the graphene oxide and the second one is the X=epoxy group. Epoxy systems can be used either as a one component epoxy system or as a two part (epoxy+hardener) system.

A one component epoxy system into which epoxy-functionalized particles (X=epoxy) contains epoxy precursor, a crosslinking catalyst such as an ionic liquid that include for example 1-ethyl-3-methylimidazolinium dicyanamide and any other additives as necessary for the intended application.

A conventional two-part epoxy adhesive consist of a part A, epoxy precursor material, and a part B, hardener. The hardener is generally a multifunctional organic amine. Suitable examples of vinyl monomers include styrene, divinyl benzene and analogues. Examples of suitable acrylates and methacrylates include methyl acrylate, methyl methacrylate, bisphenol A dimethacrylate and analogues.

Suitable epoxy-X reagents 12, may contain one or more X groups. For example, in the case of X=epoxy a trifunctional epoxy reagent has one bonding epoxy group and two X=epoxy groups that will be used at the next stage for crosslinking when dispersed in epoxy (similar structure) precursor material.

Figure 3:
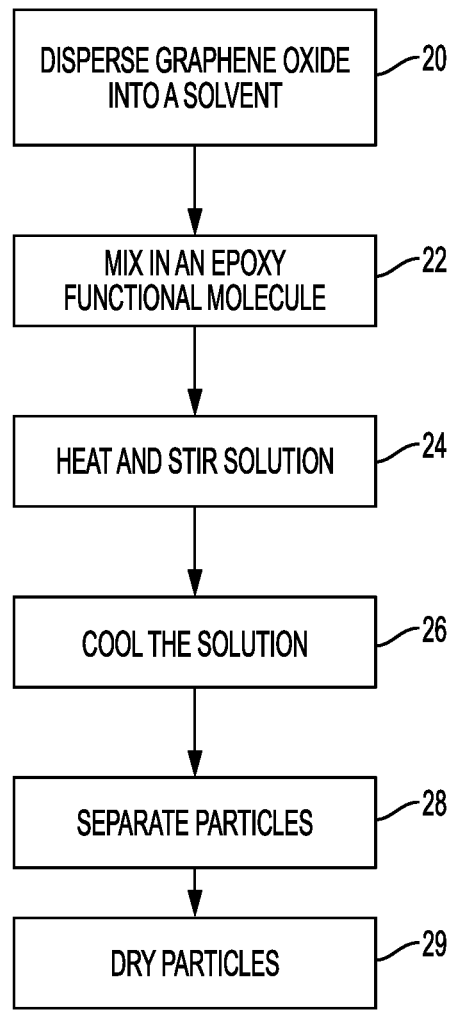
FIG. 3 shows a flowchart of an embodiment of a method of producing functionalized graphene oxide.

FIG. 3 shows a generalized example of a process to produce functionalized graphene oxide. At 20, nonfunctionalized graphene oxide is dispersed into a solvent. Graphene oxide's dispersibility is increased by the use of high shear mixing equipment, including high shear homogenizers, ball mills, and sonicators. An epoxy functional molecule is then added to the mixture at 22. An activation agent or other reagent may be added as well. The solution may then be transferred to a container more suitable for stirring and the undergoes stirring and heating at 24. The solution then cools to room temperature and it then undergoes washing with solvents and filtrating at 28 to separate the particles from solvents. Once the separated particles are dried at 29, one obtains epoxy functionalized graphene oxide (epoxy FGO). A suitable activator is for example an in organic base, such as $Ca(OH)_2$, NaOH, KOH and the like; an organic base, such as pyridine, isoquinoline, quaternary ammonium and the like; or metal salt, such as barium oxide, cobalt octate, manganese naphthenate, and the like.

The selection of the curing initiator is dictated by the type of polymer precursor and functional groups present onto the graphene oxide particles.

In one embodiment when the polymerizing or curing groups are epoxy groups, the curing initiator can be latent curing agents which initiate the curing triggered by heat, light, pressure and others, like boron trifluoride-amine complex, dicandiamide, organic-acid hydrazide, et al.; amines, like diethylenetriamine, N-aminoethylpiperazine, m-xylenediamine, diaminodiphenylmethane, polyamide resin, piperidine, et al.; imidazoles, like 2-methylimidazole, 2-ethyl-4-methylimidazole, et al.; or their derivatives, like 1-ethyl-3-methylimidazolinium dicyanamide (ionic liquid) et al.

In another embodiment when the polymerizing groups include vinyl, acrylate and methacrylate monomers, the curing initiator is a radical initiator. The radical initiator can be either a thermal radical initiator that generates reactive radicals when heated. Suitable examples include azo compounds such as azobisisobutyronitrile (AIBN) and analogues, organic peroxides such as benzoyl peroxide (BPO).

Figure 6:
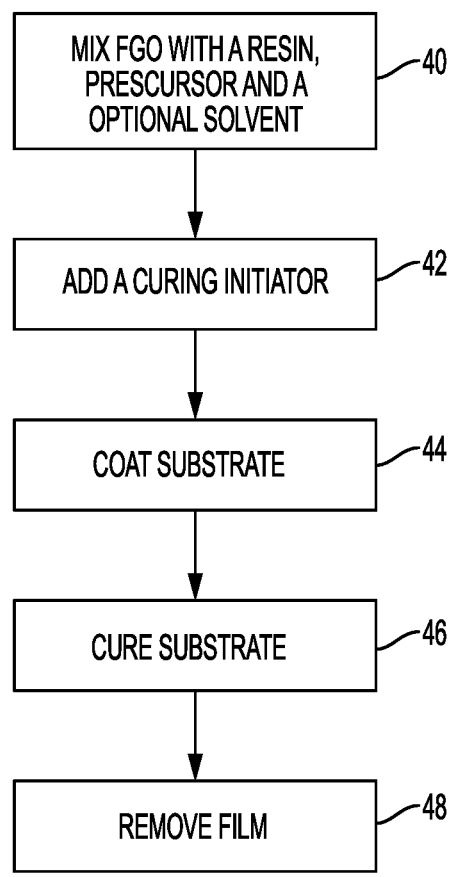
FIG. 6 shows a flowchart of an embodiment of a method of producing a cured epoxy stand-alone film using functionalized graphene oxide formulations.

FIG. 6 shows a generalized example of a process to produce stand-alone cured polymer resin using functionalized graphene oxide, by doctor blade approach.

In a different embodiment, a cured polymer resin containing functionalized graphene oxide is fabricated by depositing the formulation into a desired shape and curing the shaped formulation to form a composite having functionalized graphene oxide groups in a base polymer material. A suitable process to achieve this deposition is injection molding.

In a further different embodiment, a cured polymer resin containing functionalized graphene oxide is fabricated by extrusion through a nozzle, creation of multilayered extruded lines in order to produce a 3D printed object.

EXAMPLE 1

In a specific example, 0.5 g of GO is dispersed into 150 ml dimethyl formamide (DMF) through bath sonication. Then, 30 g of EPON™ 826, a low viscosity, light colored, liquid bisphenol A based epoxy resin, and 150 mg of calcium hydroxide $Ca(OH)_2$ were stirred into the solution. The solution was then transferred into a round flask with a reflux condenser and heated and stirred at 125° C. for 12 hours. The color of the solution turns from brown to black. After the solution cools, the solution undergoes washing and filtrating with DMF and acetone for 3 times. The resulting powder is then dried under vacuum at 125° C. overnight.

Figure 4:
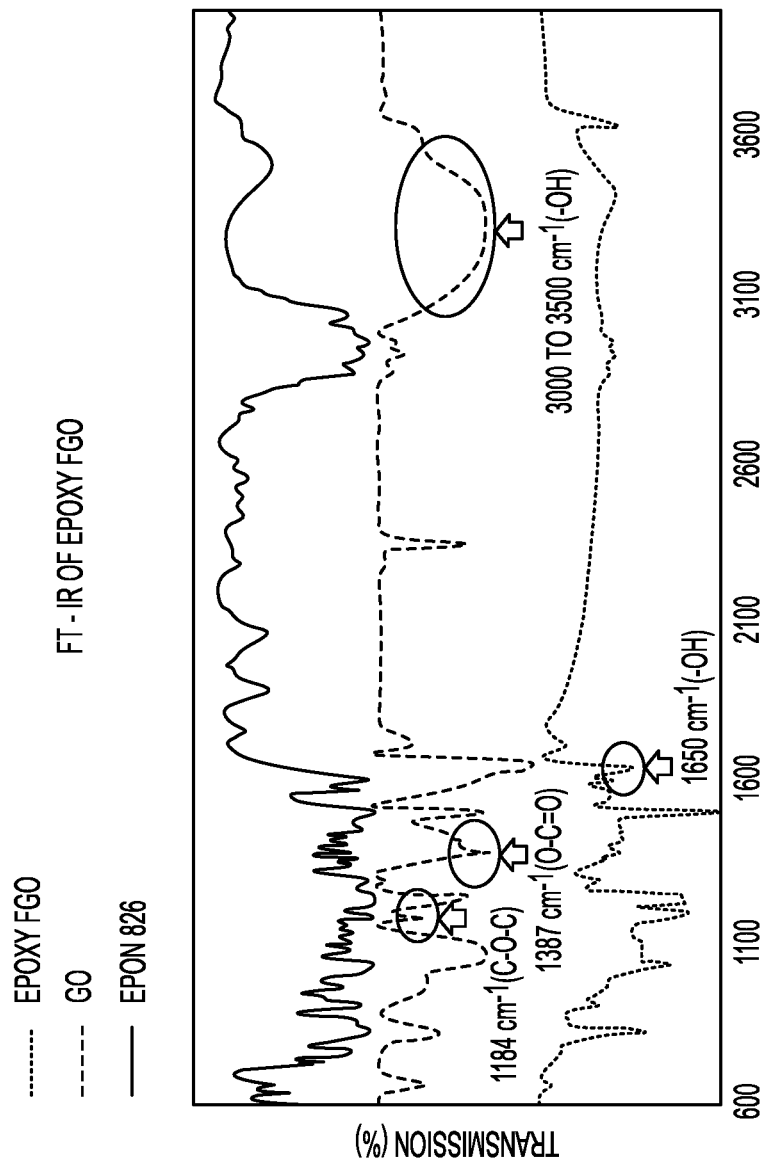
FIG. 4 shows a graph of a FT-IR spectra characterization of epoxy functionalized graphene oxide.

The incorporation of the epoxy functional groups of epoxy FGO was demonstrated by Fourier Transform Infrared Spectrum (FT-IR) spectra. As the epoxy FGO was synthesized from the GO and EPON™ 826 through the reaction between carboxyl and hydroxyl groups with epoxy groups, the reduced peak intensities at 1650 and 3000 to 3500 l/cm(—OH) and 1387 l/cm (O—C=O or C—O—H) and the increasing peak intensity at 1184 l/cm (C—O—C) demonstrate incorporation of the epoxy function groups. This is shown in FIG. 4.

Figure 5:
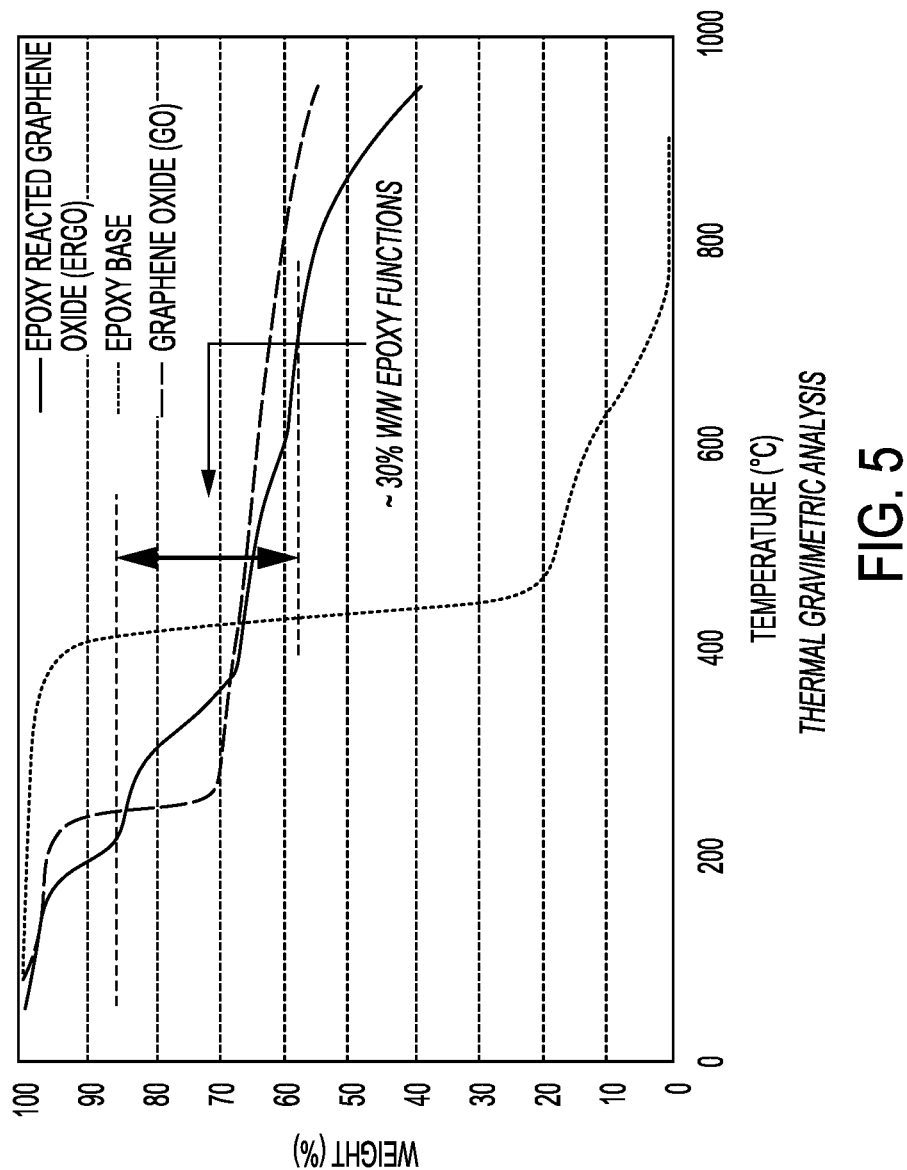
FIG. 5 shows a graph of thermal gravimetric analysis of epoxy functionalized graphene oxide.

The composition of the epoxy FGO was investigated by Thermal Gravimetric Analysis (TGA), shown in FIG. 5. GO decomposes by losing oxygen groups when heated up to about 300° C. For epoxy FGO, approximately 10 wt % is composed by the unreacted oxygen groups. EPON™ 826 loses weight in a temperature range comprised from 300° C. to 750° C. As seen in FIG. 5, epoxy FGO, approximately 30 wt % of the epoxy FGO loses weight at this temperature range. This indicates that the epoxy FGO contains approximately 30 wt % of functional molecules.

Once the epoxy FGO has been produced, it can be used to produce a cured resin film or coating product. FIG. 6 shows an embodiment of a process. At 24, the epoxy FGO is mixed with a resin precursor and an optional solvent. A curing initiator, such as anionic liquid in the case when X is an epoxy group, is added at 42. This solution was then mixed and is optionally placed under vacuum to remove air bubbles. The process then coats a substrate, such as with a doctor blade at 44. This coated substrate is then cured at 26, and the coated material was peeled off from the substrate at 28.

EXAMPLE 2

EPON™ 826 was mixed with epoxy functionalized GO (FGO), at different concentrations with 15 wt % of nanoclay and 5 wt % of dimethyl methylphosphonate (DMMP). Then, 5 wt % of a curing initiator, in this case 1-ethyl-3-methyl-imidazolinium dicyanamide, was added and mixed with a planetary mixer under vacuum. This solution was then doctor bladed onto a substrate consisting of Teflon® coated alumina substrate. The coated substrate was then cured at 100° C. for 15 hours and at 220° C. for 2 hours. The cured material was peeled off from the substrate and cut for tensile strength testing.

COMPARATIVE EXAMPLE 3

Similar cured formulations were fabricated with non-functional graphene nanoplatelets (GNP).

Figure 7:
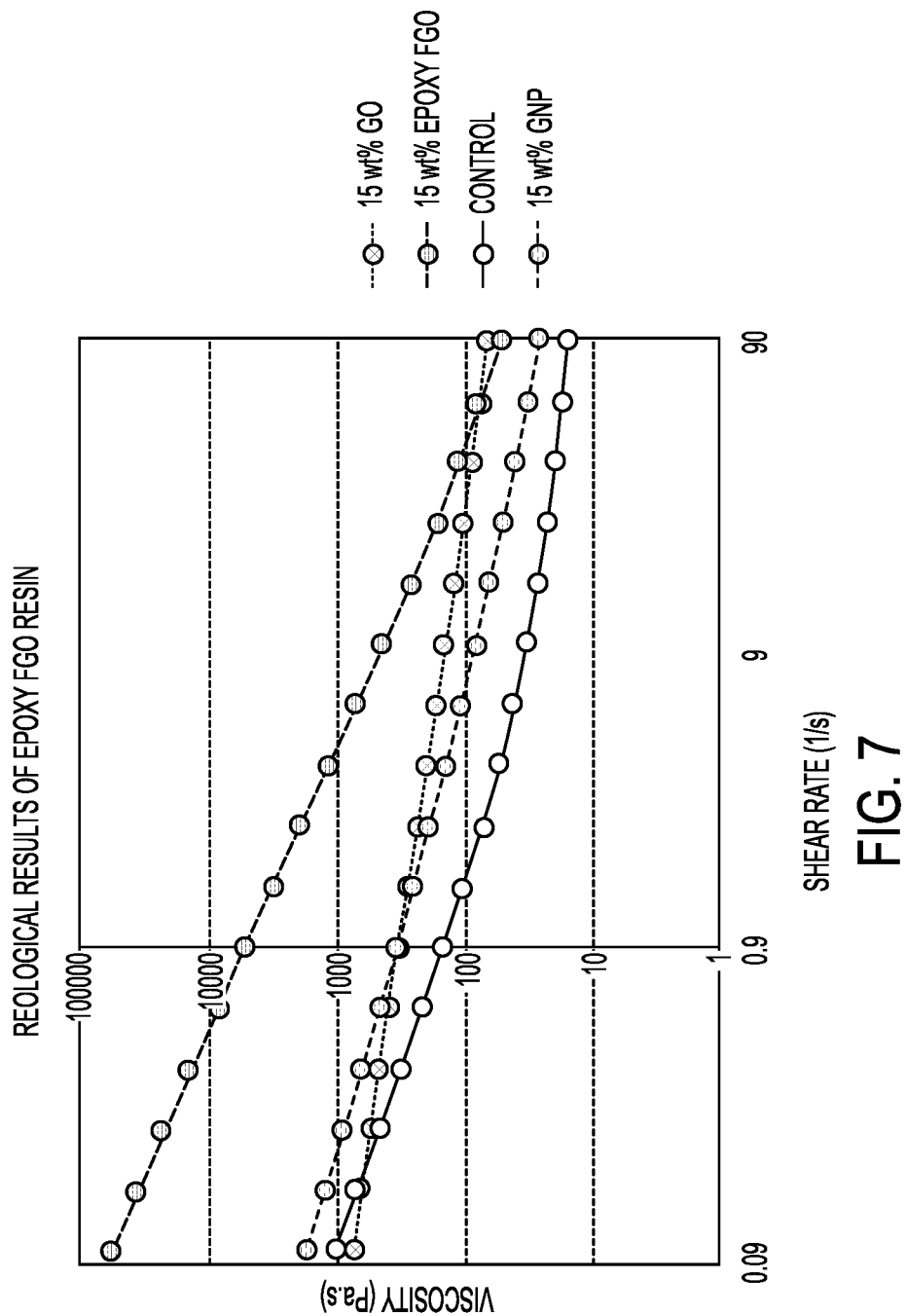
FIG. 7 shows a graph of rheological results of epoxy functionalized graphene oxide.
Figure 8:
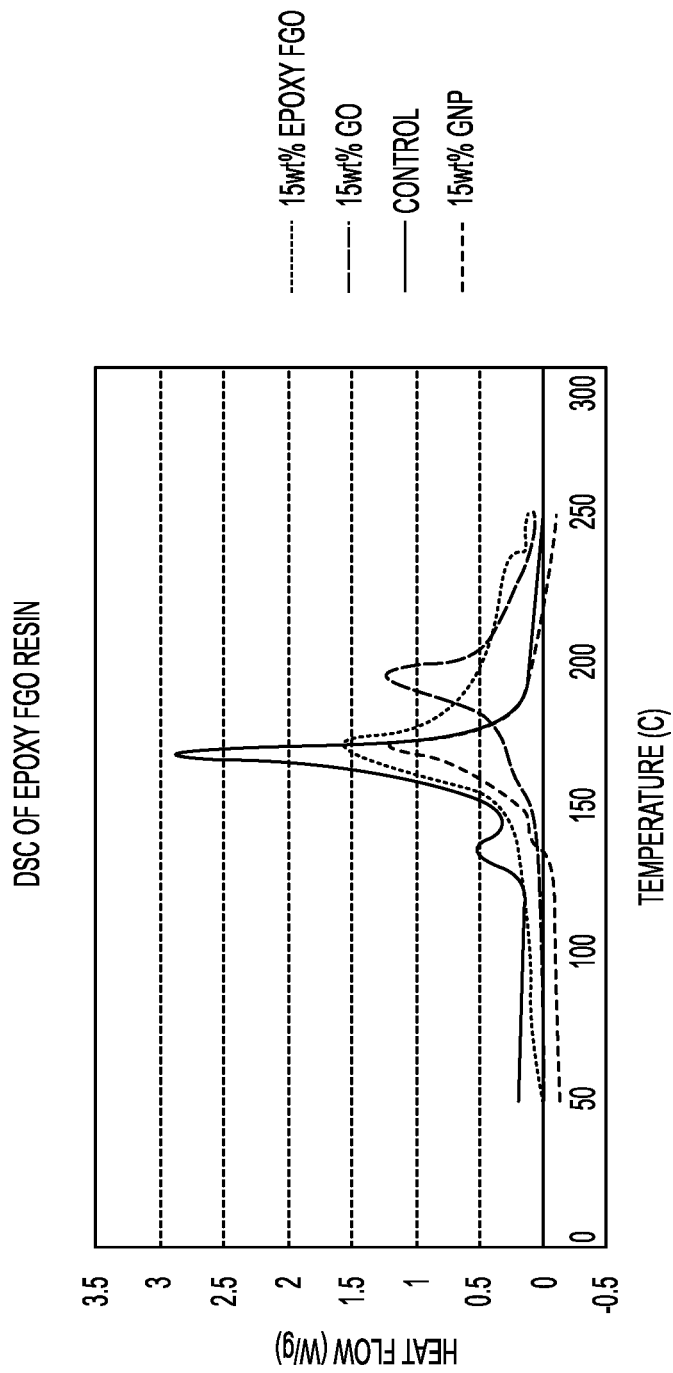
FIG. 8 shows a graph of differential scanning calorimetry analysis of epoxy graphene oxide.

For many applications, such as digital manufacturing, the printed material must maintain its shape immediately after deposition until is it cured. This requires that the formulation is high enough viscosity to hold shape, but is thixotropic, or shear thinning, to be able to be extruded during the printing process. From the rheological test results in FIG. 7, all the resins containing approximately 15 wt % of fillers in addition of 15 wt % of nanoclay and 5 wt % of DMMP show thixotropic behavior.

The Control sample was made from the same formulation, but without any fillers except 15 wt % nanoclay and 5 wt % of DMMP. For comparison, the GO and GNP are also used as fillers to demonstrate the advantage of functionalization. Most remarkably, when compared with all the other fillers tested, the formulation with epoxy FGO has the highest difference in viscosity at high and low shear rate. This performance may be explained by the good interaction between the epoxy FGO and epoxy monomer because of the similar chemical nature. This feature is not available with the other fillers tested here.

Differential Scanning Calorimetry (DSC) investigated the curing dynamic of the resin. The heat of curing directly relates to the degree of cure of the epoxy. The higher the heat of curing, the lower the activation energy and the higher the degree of cure and the stronger the cured epoxy. This experiment obtained the heat of curing by 5° C./min heating rate. The activation energy of each sample was calculated according to Kissinger model [Wei, J., Zhang, X., Qiu, J. and Weeks, B. L. (2015), Thermal kinetics and thermo-mechanical properties of graphene integrated fluoroelastomer. J. Polym. Sci. Part B: Polym. Phys., 53: 1691-1700. doi: 10.1002/polb.23890] by the peak temperature from 4 DSC heating sweeps with different heating rate from 5° C./min to 20° C./min. The summary of the heat of curing and activation energy for control, 15 wt % epoxy FGO, 15 wt % GNP and 15 wt % GO are presented in Table 1. This example demonstrated that the functional formulation accelerates the curing by decreasing the activation energy while the non, or randomly functionalized, graphene slow down the polymerization process due to increased activation energy when compared with the control materials that contains no FGO particles. As a result, more heat is needed to finish the curing which indicates higher degree of curing and crosslinking.

TABLE 1

| Sample | Control | 15 wt % GNP | 15 wt % GO | 15 wt % epoxy FGO |
| --- | --- | --- | --- | --- |
| Heat of curing (J/g) | 444.7 | 390.3 | 363.0 | 514.2 |
| Activation Energy (kJ/Mol) | 76.5 | 81.5 | 158.3 | 34.9 |

This process enables formulation with high weight concentration dispersible particles when compared to conventional graphene dispersed epoxy materials of functional groups. This formulation is resin extrudable, results in mechanically reinforced polymer composites, increases the Young's' modulus without sacrificing tensile strength, and has high flexibility with high concentration of particles.

Figure 9:
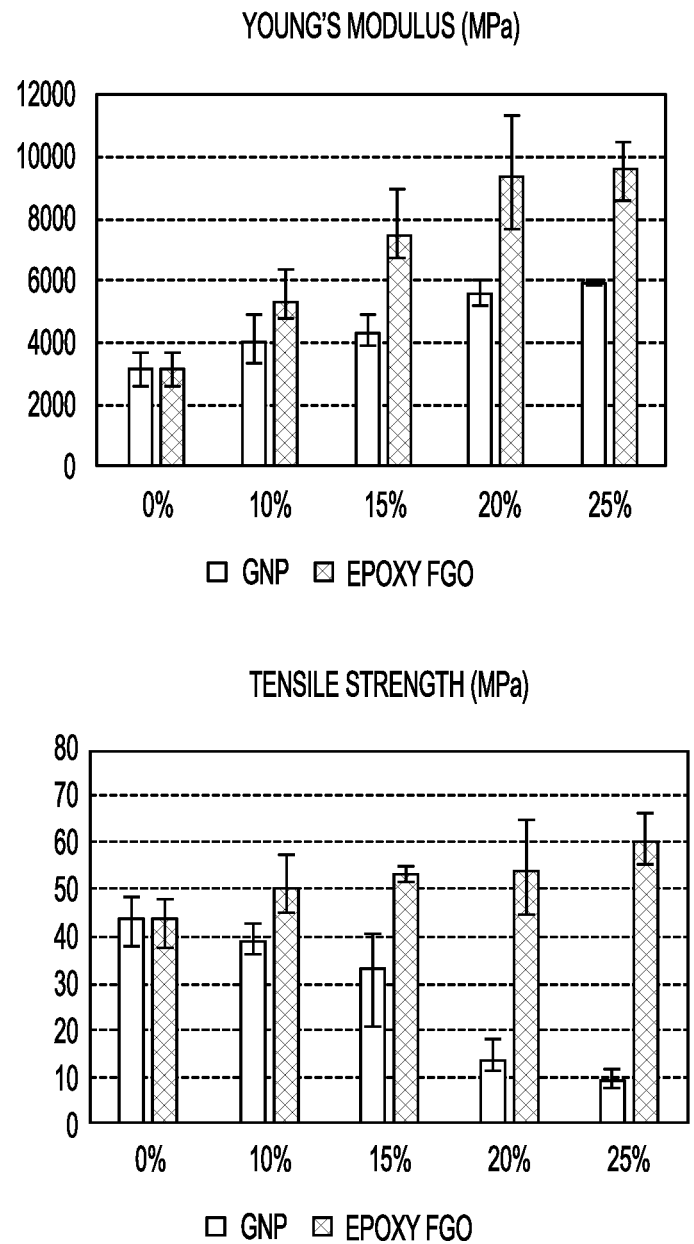
FIG. 9 shows graphical comparisons of the mechanical properties of epoxy/graphene formulations, between epoxy functionalized graphene oxide and unfunctionalized raw graphene.

Tensile test obtained the mechanical properties, of cured particle-resins formulations. The cured resins with epoxy FGO and GNP, as nonfunctional graphene, with different concentrations were tested and compared. FIG. 9 shows the Young's modulus on the left and tensile strength on the right. In summary, the results are as follows.

As expected, the addition of particle filters increased the Young's modulus of the base epoxy materials in all cases, as shown on the left. However, the enhancement obtained with epoxy FGO is approximately 2 times higher than that produced by unfunctionalized graphene (GNP). This result can be attributed to the better exfoliation of the epoxy FGO, the formation of chemically linked graphene oxide networks and to the higher degree of cure when compared to the GNP filler.

Increased concentration of the epoxy FGO resulted in increased tensile strength of about 30% when compared with the base epoxy material (no particles at all). In sharp contrast, formulations with non-functionalized graphene (GNP) showed the typical trend generally found with particle filled polymer composites, a steep decrease of the tensile strength (approximatively 5 times decrease when increasing the GNP concentration from 0% to 25%) as the concentration of the filler is increased, as seen on the right of FIG. 9.

The tensile strength almost solely depends on the interaction between filler particles and the epoxy material. With poor interaction, like in the case of GNP, higher concentration dispersion cannot be achieved due to particles aggregation. Aggregated particles act as nucleus and grow to fracture under stress. In the case of epoxy FGO, filler enhanced interaction by chemical bonding increases the tensile strength. As one of the results from the good interaction of epoxy FGO with epoxy monomer, the cured composite inherits the flexibility of the cured epoxy but with a greater than 3 times increase of the Young's modulus, as shown in FIG. 9.

It will be appreciated that variants of the above-disclosed and other features and functions, or alternatives thereof, may be combined into many other different systems or applications. Various presently unforeseen or unanticipated alternatives, modifications, variations, or improvements therein may be subsequently made by those skilled in the art which are also intended to be encompassed by the following claims.

What is claimed is:

1. A method of manufacturing a cured polymer resin using functionalized graphene oxide, comprising:
    mixing functionalized graphene oxide with a resin precursor to produce a functionalized graphene mixture, wherein the particles contain functional groups identical to a reactive precursor in the resin precursor and cure at a same time as a polymer precursor material in the resin precursor;
    adding a curing initiator to the functionalized graphene mixture and mixing to produce a formulation;
    depositing the formulation into a desired shape; and
    curing the formulation with at least one temperature of 220° C. to form a polymer having functionalized graphene oxide groups in a base polymer material.

2. The method of claim 1, wherein depositing the formulation into the desired shape comprises injection molding.

3. The method of claim 1, wherein depositing the formulation into a desired shape comprises 3D printing by extrusion through a nozzle.

4. The method of claim 1, wherein curing comprises curing at a first temperature and then curing at a second temperature of 220° C. that is higher than the first temperature.

5. The method of claim 1, wherein the desired shape is a coated film onto one of a substrate or a standalone film after substrate removal.

6. The method in claim 1, wherein the functionalized graphene oxide and resin precursor contain epoxy groups and the curing initiator is an ionic liquid.

7. The method of claim 6, wherein the resin precursor material comprises an epoxy material and the curing initiator comprises an organic amino hardener material and the first curing temperature is ambient room temperature.

8. The method as claimed in claim 1, wherein mixing the functionalized graphene oxide with a resin precursor includes mixing the functionalized graphene and the resin precursor with a solvent.

9. The method as claimed in claim 1, wherein the resin precursor is epoxy and adding the curing initiator comprises adding a latent curing agent.

10. The method as claimed in claim 9, further comprising initiating the latent curing agent.

11. The method as claimed in claim 1, wherein adding the curing initiator comprises adding a radical initiator.

12. The method as claimed in claim 11, wherein the radical initiator comprises a thermal initiator.

* * * * *